(12) United States Patent
Demarne et al.

(10) Patent No.: US 7,531,193 B2
(45) Date of Patent: May 12, 2009

(54) **USE OF AN *ACMELLA OLERACEA* EXTRACT FOR THE BOTULINUM TOXIN-LIKE EFFECT THEREOF IN AN ANTI-WRINKLE COSMETIC COMPOSITION**

(75) Inventors: Frederic Demarne, Marseilles (FR); Ghislaine Passaro, Voreppe (FR)

(73) Assignee: Gattefosse S.A.S., Saint Priest (FR)

( * ) Notice: Subject to any disclaimer, the term of this patent is extended or adjusted under 35 U.S.C. 154(b) by 217 days.

(21) Appl. No.: 10/583,931

(22) PCT Filed: Jan. 4, 2005

(86) PCT No.: PCT/FR2005/050005

§ 371 (c)(1),
(2), (4) Date: Jun. 20, 2006

(87) PCT Pub. No.: WO2005/072698

PCT Pub. Date: Aug. 11, 2005

(65) Prior Publication Data

US 2008/0069912 A1    Mar. 20, 2008

(30) Foreign Application Priority Data

Jan. 15, 2004    (FR) .................................. 04 50093

(51) Int. Cl.
*A61K 36/00* (2006.01)

(52) U.S. Cl. ...................... 424/725; 424/778

(58) Field of Classification Search .............. None
See application file for complete search history.

(56) References Cited

U.S. PATENT DOCUMENTS

| 4,014,995 | A | * | 3/1977 | Juliano et al. ............... 514/783 |
| 6,387,398 | B1 | | 5/2002 | Vollhardt et al. |
| 2004/0028643 | A1 | * | 2/2004 | Chiba et al. ................... 424/74 |

FOREIGN PATENT DOCUMENTS

| EP | 1352640 | | 10/2003 |
| JP | 60-215610 | * | 10/1985 |
| JP | 60 215610 A | | 10/1985 |
| JP | 6072858 | | 3/1994 |
| JP | 9175947 | | 7/1997 |
| WO | WO 02/47656 | * | 6/2002 |

OTHER PUBLICATIONS

Database Biosis Online! Biosciences Information Service, Philadelphia, PA, Apr. 2002, Chakraborty et al.: "Locann anaesthetic effect of Spilanthes axmella in experimental animal models".
"Food and drink additive—contg spilanthes acmella ext", Derwent, 1973.
Database Biosis Online!, Biosciences Information Service, Philadelphia, PA; 1984, Herdy G.V.H. Et al. "Effect of Spilanthol Jambu Spilanthes-Oleracea Extract on the Action Potential by Recording of an Atrial Fiber".
Stashenko E.E. et al. "Volatile secondary metabolites from Spilanthes americana obtained by simultaneous steam distillation-solvent extraction and supercritical fluid extraction", Journal of Chromatography, vol. 752, 1996, pp. 223-232.
Ansari A.H. et al. "Analgesic study of N-Isobutyl-4, 5-Decadienamide Isolated from the Flowers of Spilanthes Acmella (Murr)" Indian Journal of Pharmaceutical Sciences, vol. 50, No. 2, 1988, p. 106.
Greger H "Alkamides: Structural Relationships, Distribution and Biological Activity" Planta Medica, 1984, pp. 366-375.
Greger H et al. "New Amides from Spilanthes oleracea" Monatshefte fur Chemie, vol. 116, 1985, pp. 273-277.
Martin R. and Becker H. "Spilanthol-related amides from Acmella ciliata" Phytochemistry, vol. 23, No. 8, 1984, pp. 1781-1783.

* cited by examiner

*Primary Examiner*—Susan C Hoffman
(74) *Attorney, Agent, or Firm*—Heslin Rothenberg Farley & Mesiti PC; Andrew K. Gonsalves

(57) ABSTRACT

Spilanthol, in the form of an *Acmella oleracea* extract, inhibits contractions in subcutaneous muscles, notably those of the face, and can be used as an anti-wrinkle product. A cosmetic treatment procedure for wrinkles consists of locally or subcutaneously applying an effective quantity of a composition based on spilanthol pure or in the form of an *Acmella oleracea* extract.

15 Claims, No Drawings

USE OF AN *ACMELLA OLERACEA* EXTRACT FOR THE BOTULINUM TOXIN-LIKE EFFECT THEREOF IN AN ANTI-WRINKLE COSMETIC COMPOSITION

CROSS REFERENCE TO RELATED APPLICATIONS

This application is a 371 filing of International Application PCT/FR2005/050005 filed on Jan. 4, 2005 and published, in French, as International Publication No. WO 2005/072698 on Aug. 11, 2005, and claims priority of French Patent Application No. 04.50093 filed on Jan. 15, 2004, which applications are hereby incorporated by reference herein in their entirety.

BACKGROUND OF THE INVENTION

The invention relates to the use of spilanthol, notably in the form of an *Acemella oleracea* extract, for its botulinum toxin-like action, i.e. for its ability to inhibit contractions in subcutaneous muscles, notably those of the face. It also relates to the use of the purified molecule or of the extract in an anti-wrinkle cosmetic composition.

Botox® or botulinum toxin is a substance extracted from the bacterium called *Clostridium botulinum*. This toxin, injected into the face muscles, paralyses them, attenuating face wrinkles. It has notably been observed that Botox® is particularly effective in attenuating frown wrinkles, forehead wrinkles, crow's feet and nose crease wrinkles. The main disadvantage of Botox®however, lies in its toxicity, as its use under certain conditions can lead to death.

In other words, the problem is to develop a product that provides botulinum toxin-like properties, but without any toxicity.

In the context of his research, the Applicant observed that spilanthol, notably in the form of an *Acmella oleracea* extract, was able to effectively inhibit contractile activity in subcutaneous face muscles.

*Acmella oleracea* is a plant of the genus *Acmella* belonging to the *Compositae-Heliantheae* family identified under the numbers This plant is also known under the following names: *Spilanthus oleracea*, *Pyrethrum spilanthus*, and *Spilanthes acmella* variety *oleracea*.

*Acmella oleracea* is a small annual plant from South America measuring 40 to 60 cm in height. This fragile plant flowers year-round, producing many yellow flowers. The plant is easy to multiply with seeds and cuttings.

*Acmella oleracea* is notably used in cosmetic compositions as the source of a molecule called spilanthol.

Document JP 9175947 thus describes a composition for hair growth containing a *Spilanthes oleracea* extract as an active ingredient in fat, notably oil.

Document JP 6072858 describes a spilanthol-based composition for use as a bubble bath for its refreshing effect on the skin.

Document JP 60215610 describes a bath preparation with sedative and firming properties.

Document U.S. Pat. No. 6,387,398 describes the cosmetic use of a *Spilanthes acmella* extract, notably as a deodorant agent, for the feeling of freshness provided by *Spilanthol*.

Document EP-A-1,352,640 concerns the use of *Acmella oleracea* (Gin-New-Kou) solely for its inhibiting effect on the formation of melanin with, as an application, anti-ageing indications.

The publication by Chakraborty, "local anaesthetic effect of *Spilanthes acmella* in experimental animal models" (XP009035381), discloses the local anaesthetic effect of *Spilanthes acmella*.

The publication by Herdy, "effect of spilanthol jambu spilanthes oleracea extract on the action potential by recording of an atrial fiber" (XP002293685), stresses the ability of *Spilanthol* to generate arrhythmia when injected into isolated rabbit hearts.

The document by Stashenko, "volatile secondary metabolites from *Spilanthes americana* obtained by simultaneous distillation-solvent extraction and supercritical fluid extraction" (XP002293687), describes an extraction procedure for *Spilanthes americana* metabolites. In the introduction, it is indicated that this plant has analgesic and paralysing effects, notably when applied to the tongue.

To the Applicant's knowledge, no document on the state of the art describes the ability of spilanthol and moreover of *Acmella oleracea* to inhibit the contraction of subcutaneous muscles, notably those of the face.

SUMMARY OF THE INVENTION

In other words, the invention firstly concerns the use of spilanthol for producing a composition designed for inhibiting contractile activity in subcutaneous muscles.

Of course, for this application, spilanthol can be used locally by topical application or by injection directly into the subcutaneous muscles.

As indicated above, the Applicant observed that the use of an *Acmella oleracea* extract as the source of spilanthol gave even better results on subcutaneous muscle contraction than did pure spilanthol. As an extract, the aerial portions are used in practice, advantageously the leaves or flower buds.

Given the property on muscle fibres demonstrated in this application, the invention also relates to the use of spilanthol pure or in plant extract form, notably of *Acmella oleracea* for the production of an anti-wrinkle cosmetic composition.

When spilanthol is used in pure form, the concentration of spilanthol in the composition is between 0.005 and 10% of the weight, and advantageously between 0.05 and 5%, of the weight of the composition.

The plant extract used as the source of spilanthol can come in dry or liquid form. When it comes in dry form, it comprises between 0.005 and 20%, and advantageously between 0.1 and 10%, of the weight of the composition. When it comes in liquid form, it comprises between 0.1 and 20%, and advantageously between 0.5 and 10%, of the weight of the composition.

Extraction is performed from the whole plant or a part of the plant, notably from flower buds. The plant or part of the plant is ground in a polar solvent usable in topical cosmetic applications, and therefore in aqueous, alcoholic or glycolic media. Generally, the polar solvent is chosen from the group including water, ethanol, glycols such as propylene glycol, butylene glycol, alone or in mixtures, although ethanol remains one of the preferred solvents.

The composition according to the invention can come in all pharmaceutical forms normally used for topical application on the skin, notably in the form of an aqueous solution, an oil-in-water or water-in-oil or multiple emulsion, a silicone emulsion or microemulsion or nanoemulsion of an aqueous gel.

This composition may be more or less fluid and have an appearance of a white or coloured cream, a pomade, a milk, a lotion, a serum or a gel, etc.

The composition of the invention can contain the usual additives in the cosmetic and dermatological fields, such as fats, emulsifiers and co-emulsifiers, hydrophilic or lipophilic gelling agents, hydrophilic or lipophilic active ingredients, preservatives, antioxidants, solvents, fragrances, fillers, hydrophilic and lipophilic filters, dyestuffs, neutralisers, propenetrating agents and polymers.

The quantities of these various additives are those conventionally used in the fields in question, for example 0.01 to 30% of the total weight of the composition. These additives, depending on their nature, can be added in the fatty phase or in the aqueous phase.

The fats that can be used in the invention include mineral oils, oils of animal origin (lanolin), synthetic oils (isopropyl myristate, octyldodecyl, isostearyl isostearate, decyl oleate or isopropyl palmitate), silicone oils (cyclomethicone or dimethicone) and fluorinated oils. Fatty alcohol, fatty acids, waxes and gums, notably silicone gums and elastomers can be used as fats.

The emulsifiers and co-emulsifiers that can be used in the invention include, for example, polyglycerol fatty acid esters, sucrose fatty acid esters, sorbitane fatty acid esters, oxyethylene sorbitan fatty acid esters, PEG fatty alcohol ethers, glycerol fatty acid esters, alkyl sulphates, alkyl ether sulphates, alkyl phosphates, alkyl polyglucosides and dimethicone copolyols.

The hydrophilic gelling agents notably include carboxyvinyl polymers (carbomer), acrylic copolymers such as acrylate/alkylacrylate copolymers, polyacrylamids, polysaccharides such as xanthan gum, guar gum, natural gums such as cellulose gum and derivatives, clays and 2-acrylamido-2-methylpropane acid copolymers.

The lipophilic gelling agents include modified clays such as bentones, fatty acid metal salts, hydrophobic silica and ethylcellulose.

The cosmetic composition may also contain active ingredients. The active ingredients notably include depigmenting agents, emollients, moisturisers, anti-seborrheics, anti-acne agents, keratolytic and/or desquamating agents, draining agents, anti-irritant agents, soothing agents, slimming agents such as xanthic bases (caffeine), vitamins and their mixtures, matting agents, anti-ageing active ingredients such as retinol and anti-wrinkle agents.

If there is any incompatibility between them or with the *Acmella oleracea* extract, the active ingredients indicated above and/or the *Acmella oleracea* extract can be incorporated in spheroids, notably ionic or non-ionic vesicles and/or nanoparticles (nanocapsules and/or nanospheres), so as to isolate them from each other in the composition.

The preservatives that can be used in the invention include benzoic acid, its salts and esters; sorbic acid and its salts; parabens, their salts and esters; triclosan; imidazolidinyl urea; phenoxyethanol; DMDM hydantoin; diazolidinyl urea and chlorphenesin.

The antioxidants that can be used in the invention include chelating agents such as EDTA and its salts.

The solvents that can be used in the invention include, as mentioned above, water, ethanol, glycerine, propylene glycol, butylene glycol and sorbitol.

The fillers that can be used in the invention include talc, kaolin, mica, serecite, magnesium carbonate, aluminium silicate and organic powders such as nylon.

The filters that can be used in the invention include conventionally used UVA and UVB filters such as benzophenone-3, butyl methoxydibenzoyl methane, octocrylene, octyl methoxycinnamate, 4-methylbenzylidene camphor, octyl salicylate, terephthalylidene dicamphor sulfonic acid and drometrizole trisiloxane. We can also mention the physical filters $TiO_2$ and ZnO in their micrometric and nanometric forms.

The dyestuffs that can be used in the invention include lipophilic dyes, hydrophilic dyes, pigments and mother-of-pearl commonly used in cosmetic or dermatological compositions, and their mixtures.

The neutralisers that can be used in the invention include soda, triethanolamine, aminomethyl propanol and potassium hydroxide.

The propenetrating agents that can be used in the invention include alcohols and glycols (ethanol and propylene glycol), ethoxydiglycol, alcohols and fatty acids (oleic acid), fatty acid esters and dimethyl isosorbide.

The invention also relates to the use of the composition containing spilanthol pure or in the form of an *Acmella oleracea* extract as an anti-wrinkle product. It also relates to the cosmetic treatment of wrinkles by local or subcutaneous application, using an effective quantity of a cosmetic composition based on pure spilanthol or in the form of *Acmella oleracea* extract.

DETAILED DESCRIPTION

The invention and the resulting advantages can be seen in the following examples of embodiments backed up by the appended figures.

EXAMPLE 1

Production of an *Acmella oleracea* Extract

The whole dry plant comes from South America or more generally from tropical countries. This plant is ground until a powdered is obtained.

The extraction of the ground plant is performed in a mixture of ethanol at 96.2° $H_2O$ (80/20); volume/volume at ambient temperature subjected to magnetic stirring and protected from light, for 6 hours.

The extract is then filtered through a nylon filter then through a cellulose membrane (to 0.22 microns). In example 2, it is then lyophilised to be used diluted to 50% in maltodextrine.

EXAMPLE 2

1. Objective of the Study

To assess the ability of purified spilanthol and an *Acmella oleracea* extract to produce a reversible blockage of muscular contractions.

2. General Methodology

Nerve-muscle Model

Nerve-muscle co-culture is a culture model which is used to recreate human striated muscle cell innervation with spinal cord and spinal ganglion explants from rat embryos. After 21 days of culture, the muscle fibres formed contract spontaneously.

The nerve-muscle co-culture model is a model suited to studying the influence of a substance on muscle contraction frequency, as well as to studying the recuperation of contractile activity after blockage of muscle contractions by a substance.

Carisprodol at 1 mM is used as a positive control for reversible blockage of muscle contractions.

Measurement of the Frequency of Contractions

For each selected culture well, a muscle fibre showing regular contractions is referenced.

Using automated counting software, the number of contractions is counted for 30 seconds for each measurement period: before incubation (pre-incubation frequency), during incubation and during the contractile activity recuperation phase after elimination of the substance.

Interpretation of the Results

Each measure was taken in triplicate (in 3 different wells) and an activity is considered to be significant when at least 2 fibres out of 3 show the same effect according to the following modulation range:

When the frequency of contractions is greater than 120% of the pre-incubation frequency before adding the substance, we speak of an increase in the frequency of contractions, indicated by +. When the frequency becomes too high to be measurable, we speak of vibration, indicated by Vib.

When the frequency of contractions is between 80% and 120% compared to the pre-incubation frequency before adding the substance, it is not modified and is indicated by 0.

When the frequency of contractions is less than 80% of the pre-incubation frequency before adding the substance, we speak of a decrease in the frequency of contractions, indicated by—or block (blockage) if it is 0%.

We speak of complete recuperation of contractile activity after blockage when at least 2 fibres out of 3 return to a frequency of contraction greater than or equal to 80% of the pre-incubation frequency of contraction, indicated by +.

We speak of incomplete recuperation of contractile activity after blockage when at least 2 fibres out of 3 return to a frequency of contraction between 10 and 80% of the pre-incubation frequency of contraction, indicated by +/−.

3. Substances Studied

Nature and origin of the substance:

Lyophilised extract of the aerial portions (containing flower buds) of *Acmella oleracea* diluted to 50% in maltodextrine.

Spilanthol purified to 97% from an *Acmella oleracea* extract.

4. Study Process a/ Pure Spilanthol

The frequency of contraction is determined after 5 minutes, 1 hour and 6 hours of incubation with the substance. At 6 hours, the substance is eliminated and recuperation of contractile activity is studied 1 hour and 24 hours later.

b/ *Acmella oleracea* Extract

The frequency of contraction is determined (at 5 minutes, 1 hour and 6 hours) until a blockage of contractions is obtained with the substance. Once blockage is achieved, the substance is eliminated and recuperation of contractile activity is studied at 1 hour, 4 hours and 24 hours.

5. Results

Pure Spilanthol

| | | Frequency of contractions (%) | | | | | Interpretation | | | | |
|---|---|---|---|---|---|---|---|---|---|---|---|
| | | Incubation without washout | | | Recuperation after washout | | Incubation without washout | | | Recuperation after washout | |
| Substance | [C] | 5 min | 1 h | 6 h | 1 h | 24 h | 5 min | 1 h | 6 h | 1 h | 24 h |
| Pure spilanthol | $40 \times 10^{-5}\%$ | 0 | 0 | 0 | 0 | 0 | block | block | block | block | block |
| | | 0 | 0 | 0 | 0 | 37 | block | block | block | block | +/− |
| | | 0 | 0 | 0 | 0 | 0 | block | block | block | block | block |
| | $160 \times 10^{-5}\%$ | 0 | 0 | 0 | 0 | 0 | block | block | block | block | block |
| | | 7 | 0 | 4 | 0 | 0 | − | block | − | block | block |
| | | 0 | 0 | 0 | 0 | 0 | block | block | block | block | block |

At the concentrations ($40 \times 10^{-5}\%$ and $160 \times 10^{-5}\%$), pure spilanthol blocks muscle contractions after 5 minutes of incubation. The blockage is maintained until 6 hours and the fibres remain blocked for 24 hours after elimination of the substance.

*Acmella oleracea* Extract

| | | Frequency of contractions (%) | | | | | | Interpretation | | | | | |
|---|---|---|---|---|---|---|---|---|---|---|---|---|---|
| | | Incubation without washout | | | Recuperation after washout | | | Incubation without washout | | | Recuperation after washout | | |
| Substance | [C] | 5 min | 1 h | 6 h | 1 h | 4 h | 24 h | 5 min | 1 h | 6 h | 1 h | 4 h | 24 h |
| Extract | $600 \times 10^{-5}\%$ | Vib | 0 | 0 | 114 | Not tested | | + | block | block | + | Not tested | |
| | | Vib | Vib | 0 | 171 | | | + | + | block | + | | |
| | | 400 | Vib | Vib | 194 | | | + | + | + | + | | |
| | $1,200 \times 10^{-5}\%$ | 0 | Not tested | | 47 | Not tested | | block | Not tested | | +/− | Not tested | |
| | | 5 | | | 104 | | | − | | | + | | |
| | | 0 | | | 110 | | | block | | | + | | |
| | $2,400 \times 10^{-5}\%$ | 63 | Not tested | | 97 | Not tested | | − | Not tested | | + | Not tested | |
| | | 0 | | | 145 | | | block | | | + | | |
| | | 0 | | | 126 | | | block | | | + | | |

At a concentration of $600\times10^{-5}\%$, the extract blocks the frequency of contraction of muscle fibres after 6 hours of incubation. After washout of the cultures, the muscle fibres totally recuperate their contractile activity in 1 hour.

At concentrations of $1,200\times10^{-5}\%$ and $2,400\times10^{-5}\%$, the extract blocks the frequency of contraction of muscle fibres after 5 minutes of incubation. After washout of the cultures, the muscle fibres totally recuperate their contractile activity in 1 hour.

6. Conclusion

Under the conditions of the study, the *Acmella oleracea* extract and the spilanthol compound lead to a blockage of muscle contractions. Recuperation of contractile activity is observed in presence of the plant extract but not observed in presence of spilanthol. This difference should probably be attributed to a difference in the protocol since the nerve-muscle system was only incubated for 5 minutes in presence of the extract compared to 6 hours in presence of pure spilanthol.

The anti-wrinkle effect of botulinum toxin lies in its ability to inhibit subcutaneous muscle contractions considered to be responsible for expression lines (deep wrinkles); the substances tested, given their ability to inhibit contractile activity (or botox-like effect), have the same anti-wrinkle potential as botulinum toxin.

EXAMPLE 3

Anti-wrinkle Day Cream

| Composition | Quantity (%) |
|---|---|
| Steareth-21 | 2.00 |
| Steareth-2 | 3.00 |
| Stearic acid | 1.00 |
| Cyclopentasiloxane | 3.00 |
| Octyldodecyl myristate | 2.00 |
| Cetylic alcohol | 1.00 |
| Glycerol stearate | 0.50 |
| Octyl methoxycinnamate | 5.00 |
| Benzophenone-3 | 2.00 |
| Aluminium starch octenylsuccinate | 3.00 |
| Phenoxyethanol, Methylparaben, Butylparaben, Ethylparaben, Propylparaben | 1.00 |
| Carbomer | 0.15 |
| Xanthan gum | 0.30 |
| Disodium EDTA | 0.05 |
| Glycerine | 3.00 |
| Sodium hydroxide (10% solution) | 0.30 |
| Dry *Acmella oleracea* extract | 2.00 |
| Ethanol | 3.00 |
| Tocopherol acetate | 0.50 |
| Fragrance | 0.40 |
| Water | to 100 |

Make-up Foundation

| Composition | Quantity (%) |
|---|---|
| Glycerol Stearate, Propylene Glycol Stearate, Glycerol Isostearate, Propylene Glycol Isostearate, Oleth-25, Ceteth-25 | 5 |
| Glycerol Dibehenate, Tribehenin, Glycerol Behenate | 1 |
| Ethoxydiglycol oleate | 7.5 |
| Isostearyl isostearate | 5 |
| Cetearyl alcohol | 2 |
| Dimethicone | 5 |
| Tocopheryl Acetate | 0.5 |

| Composition | Quantity (%) |
|---|---|
| Phenoxyethanol, Methylparaben, Ethylparaben, Propylparaben, Isobutylparaben | 0.6 |
| Xanthan gum | 0.4 |
| Microcrystalline cellulose, cellulose gum | 1.5 |
| Titanium dioxide | 6.6 |
| Metal oxides (yellow pigment) | 1.55 |
| Metal oxides (red pigment) | 0.43 |
| Metal oxides (black pigment) | 0.11 |
| Ethoxydiglycol oleate | 2.5 |
| Dimethicone, Dimethiconol | 3 |
| Alcohol | 5 |
| Dry *Acmella oleracea* extract | 2 |
| Water | to 100 |

O/W Emulsion

| Composition | Quantity (%) |
|---|---|
| Phenoxyethanol, Methylparaben, Butylparaben, Ethylparaben, Propylparaben | 1 |
| Carbomer | 0.4 |
| Glycerine | 3 |
| Xanthan gum | 0.1 |
| Polysorbate-60 | 0.9 |
| Glyceryl Stearate, PEG-100 Stearate | 2.1 |
| Cetyl Alcohol | 2.6 |
| Paraffin Oil | 7.5 |
| Isopropyl Myristate | 7.5 |
| Ethoxydiglycol | 5 |
| Dry *Acmella oleracea* extract | 1 |
| Fragrance | 0.2 |
| Triethanolamine | 0.3 |
| Water | to 100 |

W/O Emulsion

| Composition | Quantity (%) |
|---|---|
| Glycerine | 3 |
| Propylene Glycol, Diazolidinyl Urea, Methylparaben, Propylparaben | 1 |
| Magnesium Sulphate | 0.7 |
| Cetyl Dimethicone Copolyol | 2.5 |
| Isohexadecane | 5 |
| Caprylic/Capric Triglyceride | 5 |
| Dimethicone | 5 |
| Alcohol | 5 |
| Dry *Acmella oleracea* extract | 2 |
| Fragrance | 0.1 |
| Water | to 100 |

Microemulsion

| Composition | Quantity (%) |
|---|---|
| PEG-8 Caprylic/Capric Glycerides | 13.33 |
| Polyglyceryl-6 Dioleate | 8.67 |
| Isostearyl isostearate | 4 |
| Cyclomethicone | 2.3 |
| Diisopropyl Adipate | 1.6 |
| Octyldodecanol | 2 |
| PPG-5 Ceteth-20 | 2 |
| Phenoxyethanol, Methylparaben, Butylparaben, Ethylparaben, Propylparaben | 0.4 |

-continued

| Composition | Quantity (%) |
| --- | --- |
| Ethoxydiglycol | 2 |
| Dry *Acmella oleracea* extract | 1 |
| Water | to 100 |

W/O/W Multiple Emulsion

| Composition | Quantity (%) |
| --- | --- |
| PEG-30 Dipolyhydroxystearate | 2.4 |
| Isohexadecane | 9 |
| PPG-15 Stearyl Ether | 4.5 |
| Caprylic/Capric Triglyceride | 4.5 |
| Magnesium Sulphate | 0.82 |
| Propylene Glycol, Diazolidinyl Urea, Methylparaben, Propylparaben | 1.2 |
| Dry *Acmella oleracea* extract | 2 |
| Poloxamer 407 | 2 |
| Glycerine | 3 |
| Xanhan gum | 0.7 |
| Fragrance | 0.2 |
| Water | to 100 |

The invention claimed is:

1. A method for removing wrinkles of the face, said method comprising applying an anti-wrinkle composition containing spilanthol to facial tissue, wherein the composition is effective to remove wrinkles by inhibiting contractile activity in subcutaneous muscles of the face, and wherein said facial tissue comprises wrinkles selected from the group consisting of frown wrinkles, forehead wrinkles, crow's feet, and nose crease wrinkles.

2. The method according to claim 1, wherein said applying includes at least one of topical application and subcutaneous application.

3. The method according to claim 2, wherein said applying comprises topical application.

4. The method according to claim 2, wherein said applying comprises subcutaneous application.

5. The method according to claim 2, wherein said applying comprises both topical application and subcutaneous application.

6. The method according to claim 1, wherein said composition containing spilanthol comprises an *Acmella oleracea* extract.

7. The method according to claim 3, wherein said *Acmella oleracea* extract is an extract of *Acmella oleracea* flower buds.

8. The method according to claim 6, wherein said *Acmella oleracea* extract is an aqueous, alcoholic or mixed aqueous/alcoholic extract of *Acmella oleracea* flower buds.

9. The method according to claim 1, wherein said anti-wrinkle composition comprises 0.005 weight (wt) % to 20 wt % of dry *Acmella oleracea* extract.

10. The method according to claim 1, wherein said anti-wrinkle composition comprises 0.1 weight (wt) % to 20 wt % of liquid *Acmella oleracea* extract.

11. The method according to claim 1, wherein said anti-wrinkle composition includes 0.05 wt % to 5 wt % of spilanthol.

12. The method according to claim 1, wherein said wrinkles comprise frown wrinkles.

13. The method according to claim 1, wherein said wrinkles comprise forehead wrinkles.

14. The method according to claim 1, wherein said wrinkles comprise crow's feet.

15. The method according to claim 1, wherein said wrinkles comprise nose crease wrinkles.

* * * * *